United States Patent
Arcot et al.

(10) Patent No.: US 10,806,337 B2
(45) Date of Patent: Oct. 20, 2020

(54) ENDOSCOPE LENS CLEANING DEVICE

(71) Applicant: InVizon Technologies LLC, St. Louis, MO (US)

(72) Inventors: Kashyap Arcot, Gurnee, IL (US); William Johnston, St. Louis, MO (US); Zohny Zohny, St. Louis, MO (US); Shweta Ravi, Westerville, OH (US)

(73) Assignee: InVizon Technologies LLC, St. Louis, MO (US)

( * ) Notice: Subject to any disclaimer, the term of this patent is extended or adjusted under 35 U.S.C. 154(b) by 277 days.

(21) Appl. No.: 15/816,407

(22) Filed: Nov. 17, 2017

(65) Prior Publication Data

US 2018/0116496 A1    May 3, 2018

Related U.S. Application Data

(60) Provisional application No. 62/527,585, filed on Jun. 30, 2017.

(51) Int. Cl.
| | |
|---|---|
| *A61B 1/00* | (2006.01) |
| *A61B 90/70* | (2016.01) |
| *A61B 1/12* | (2006.01) |
| *G02B 23/24* | (2006.01) |
| *A61B 17/00* | (2006.01) |
| *H01L 31/0392* | (2006.01) |

(52) U.S. Cl.
CPC .......... *A61B 1/126* (2013.01); *A61B 1/00087* (2013.01); *A61B 1/00098* (2013.01); *A61B 1/00135* (2013.01); *A61B 17/00234* (2013.01); *A61B 90/70* (2016.02); *H01L 31/03926* (2013.01); *A61B 1/00142* (2013.01); *A61B 2090/701* (2016.02); *G02B 23/2476* (2013.01)

(58) Field of Classification Search
CPC ... A61B 90/70; A61B 2090/701; A61B 1/126; A61B 1/00135; A61B 1/00142; A61B 1/00087; A61B 17/00234; A61B 1/00098
See application file for complete search history.

(56) References Cited

U.S. PATENT DOCUMENTS

| | | | |
|---|---|---|---|
| 9,486,129 B2* | 11/2016 | Rodriguez Sanjuan | ...................... A61B 1/122 |
| 9,763,567 B2* | 9/2017 | O'Prey | ................... A61B 1/126 |
| 2003/0139649 A1* | 7/2003 | Kasahara | ............ A61B 1/00087 600/157 |
| 2014/0261545 A1* | 9/2014 | Jenkins | .............. A61B 1/00135 134/8 |
| 2014/0275787 A1* | 9/2014 | Miyamoto | ............. A61B 1/005 600/139 |
| 2015/0201826 A1* | 7/2015 | Hsu | ..................... A61B 1/00135 600/121 |

* cited by examiner

*Primary Examiner* — John P Leubecker
*Assistant Examiner* — Minqiao Huang
(74) *Attorney, Agent, or Firm* — Husch Blackwell LLP

(57) ABSTRACT

The present device is designed to enhance the efficiency of endoscopic surgeries by allowing for in situ cleaning of the lens via a combination of fluid flow and wiping mechanisms. By removing the need for intermittent halts in surgery, this device may provide a more seamless and fluid operation process, enhancing surgeon convenience and contributing to patient safety by providing a more consistent and clearer field of view for surgeons to operate in.

20 Claims, 3 Drawing Sheets

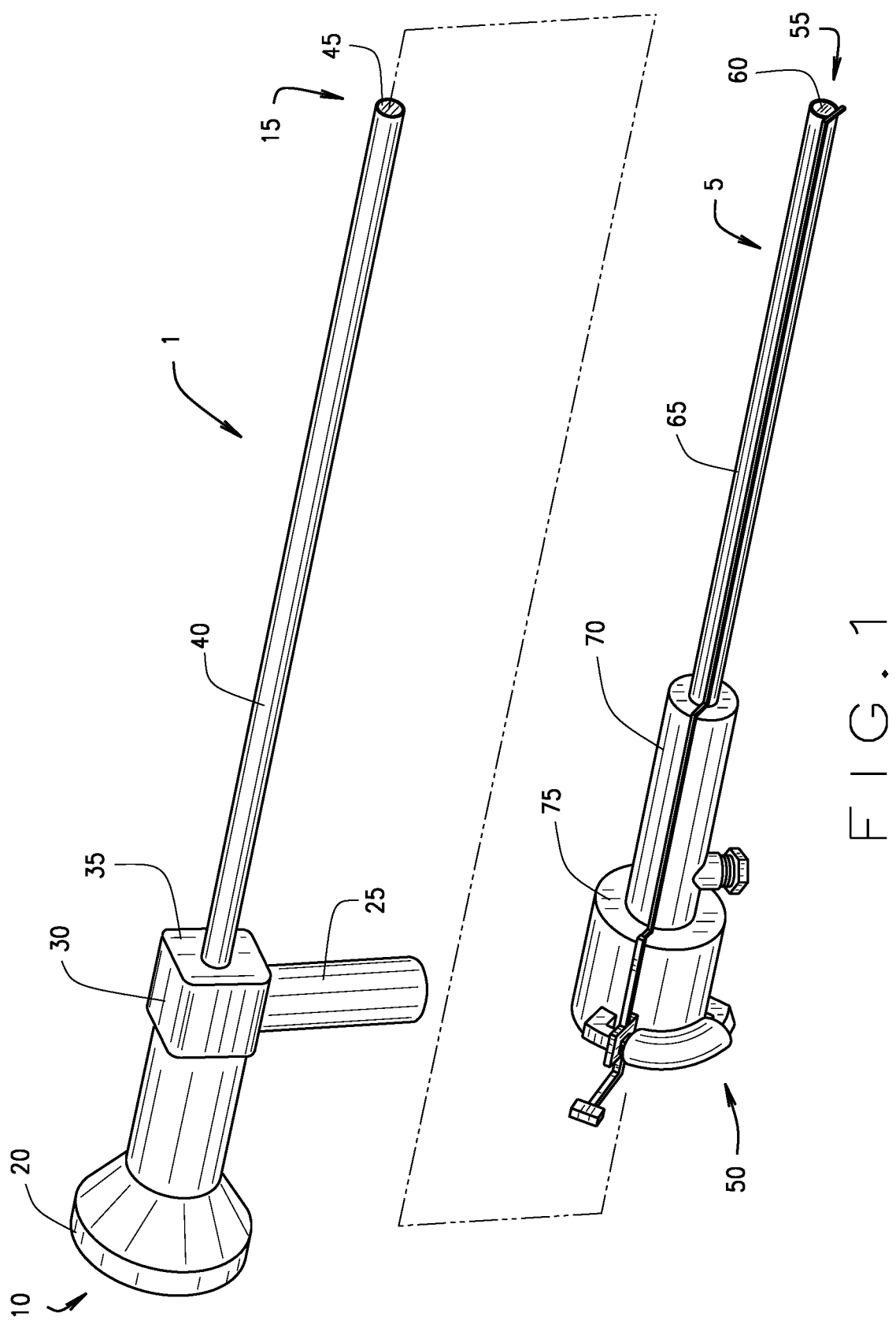

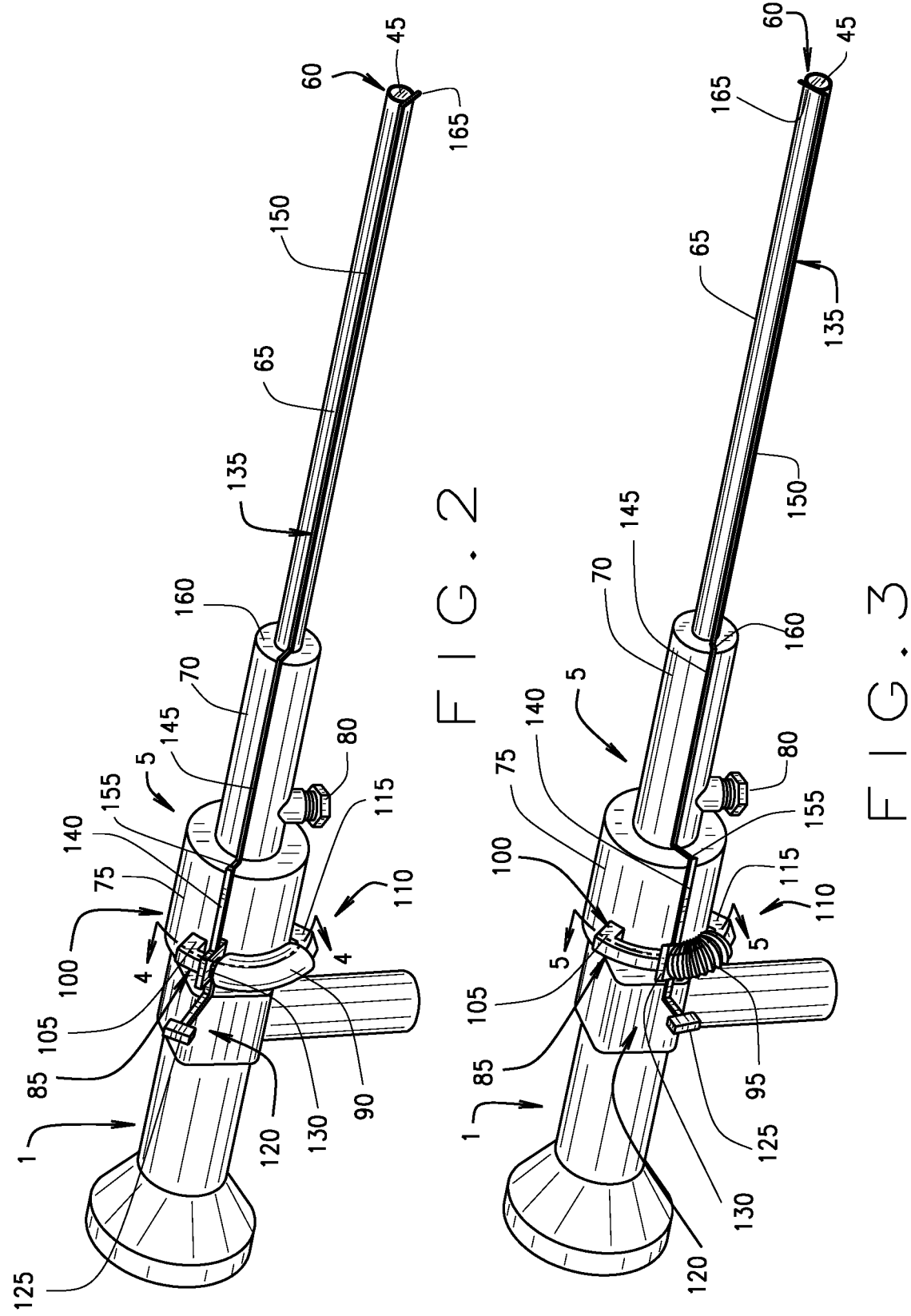

ENDOSCOPE LENS CLEANING DEVICE

CROSS-REFERENCE TO RELATED APPLICATIONS

This application claims the benefit of U.S. Provisional Application No. 62/527,585, filed Jun. 30, 2017, which is hereby incorporated by reference in its entirety.

FIELD OF THE INVENTION

The described invention relates to the field of minimally invasive surgery. Specifically, the invention relates to a cleaning device that may be coupled to an endoscope to clean the endoscope's lens and thus reduce the frequency with which a surgeon must clean an endoscope lens.

BACKGROUND OF INVENTION

Endoscopes are widely used as visualization instruments during minimally invasive surgery. Through the use of optical fibers and light transmission, endoscopes generate clear images of extremely small areas inside of patients during surgery. This allows surgeons to effectively conduct complicated procedures in confined areas without compromising visibility. Thus the area of operation is reduced, resulting in a safer procedure and faster recovery for the patient. However, during surgery the endoscope lens attracts numerous visual obstructions. These include (but are not limited to) blood, mucosa, tissue, and condensation. These obstructions must be removed in order to safely and effectively continue the operation.

Currently, the most common form of cleaning the endoscope lens in situ is to attach an irrigation sheath that flushes saline over the lens when a pedal located near the surgeon's feet is pressed. This mechanism commonly consists of two parts: a sheath and accompanying instrumentation. The sheath is attached to the endoscope lens, and contains a connecting tube that is hooked up to the instrumentation. This instrumentation flushes and suctions saline through the tube, into the sheath, and over the lens to rinse off any obstructions in the most efficient way possible.

Irrigation methods of cleaning the endoscope lens work well in some cases but are not always sufficient to clean the lens. Consequently, the surgeon must frequently stop the surgery in order to remove the endoscope from the patient's body and manually clean the lens with a cloth. There is currently no mechanical solution that can manually wipe the lens in situ without requiring removal of the endoscope from the patient. It follows that there is no such device that allows the surgeon to mechanically wipe the lens without notably changing his initial grip of the endoscope or the position of the endoscope.

SUMMARY OF INVENTION

An endoscope cleaning device is provided that combines fluid flow and wiping in order to remove obstructions from the lens in situ, thus reducing the need for intermittent halts in surgery and removal of the endoscope for manual wiping of the lens. The surgeon can preferably use the mechanism while maintaining their standard grip of the endoscope.

A variety of endoscope types may be used in conjunction with the endoscope lens cleaning device. The endoscope lens cleaning device is designed, like a sheath, to slide over an endoscope. When the cleaning device is fully slid over the endoscope, an opening in the endoscope sheath is in substantial alignment with the distal lens of the endoscope.

The cleaning device is preferably provided with an irrigation port somewhere along its longitudinal body. That irrigation port is in communication with an irrigation source (as such irrigation ports are known and understood in the art) at a first end. A small space is provided between the endoscope and the cleaning device that is in communication with a second end of the irrigation port. That space extends all the way to the distal portions of the endoscope and the cleaning device. When the irrigation source is activated, a saline or other sterile fluid may be pumped by the irrigation source through the port and along the space provided between the endoscope and cleaning device. The fluid then preferably exits the space between the endoscope and cleaning device near the distal lens of the endoscope. When fluid is released to a surgical site, it preferably increases the efficacy of the wiping mechanism described herein below.

Near a proximal portion of the cleaning device, a support rail is preferably provided that projects outwardly from the cleaning device. On the support rail, at least one of an elastic member (such as a spring) and an elastic sleeve are provided. If both are present, the sleeve preferably surrounds the elastic member to protect the elastic member from debris. The elastic member and/or elastic sleeve are preferably held securely in place at a lower end. At an upper end, an actuator is provided that preferably is slid over the support rail to compress the elastic member and/or elastic sleeve when the actuator is depressed by an operator. A toggle switch may be provided with the actuator to help an operator, such as a surgeon, activate the actuator.

The actuator is preferably provided with a rod that extends longitudinally from the actuator to the distal end of the cleaning device. Depending on the configuration of the cleaning device (to match the configuration of the endoscope), the rod may take on a number of shapes and sizes. In any embodiment, the distal end portion of the rod is preferably provided with a wiper member that extends inwardly therefrom. The wiper member, which may be made of a material such as silicon, preferably lies substantially flush with the distal lens of the endoscope and the open end portion at the distal end of the cleaning device. The wiper member preferably has a diameter that is greater than the diameter of the distal lens of the endoscope. That way, when the wiper member is activated using the below described mechanism, the wiper member slides over the opening of the cleaning device and sufficiently covers the distal lens.

When an operator presses downwardly on the toggle switch to also compress the actuator, the rod is rotated, such as in a counter-clockwise direction. When the rod is rotated, the wiper member also preferably rotates so that it sweeps across the distal lens and preferably wipes away debris and fluid from the distal lens. When an operator releases the toggle switch, the tension in the elastic member and/or sleeve preferably pushes the actuator to its original, resting position. Thus, the rod and wiper member also may return to their resting positions. As this occurs, the wiper member preferably wipes over the distal lens a second time so that additional debris may be removed from the distal lens. The operator may intermittently activate the irrigation source (as described above) to further assist in cleaning the distal lens of the endoscope.

DESCRIPTION OF DRAWINGS

FIG. 1 is an exploded view of an endoscope and endoscope lens cleaning device constructed according to the teachings of the present invention;

FIG. 2 is a perspective view of the endoscope lens cleaning device of FIG. 1 in a resting position;

FIG. 3 is a perspective view of the endoscope lens cleaning device of FIGS. 1 and 2 in an activated position;

DETAILED DESCRIPTION OF THE INVENTION

Figure 4:
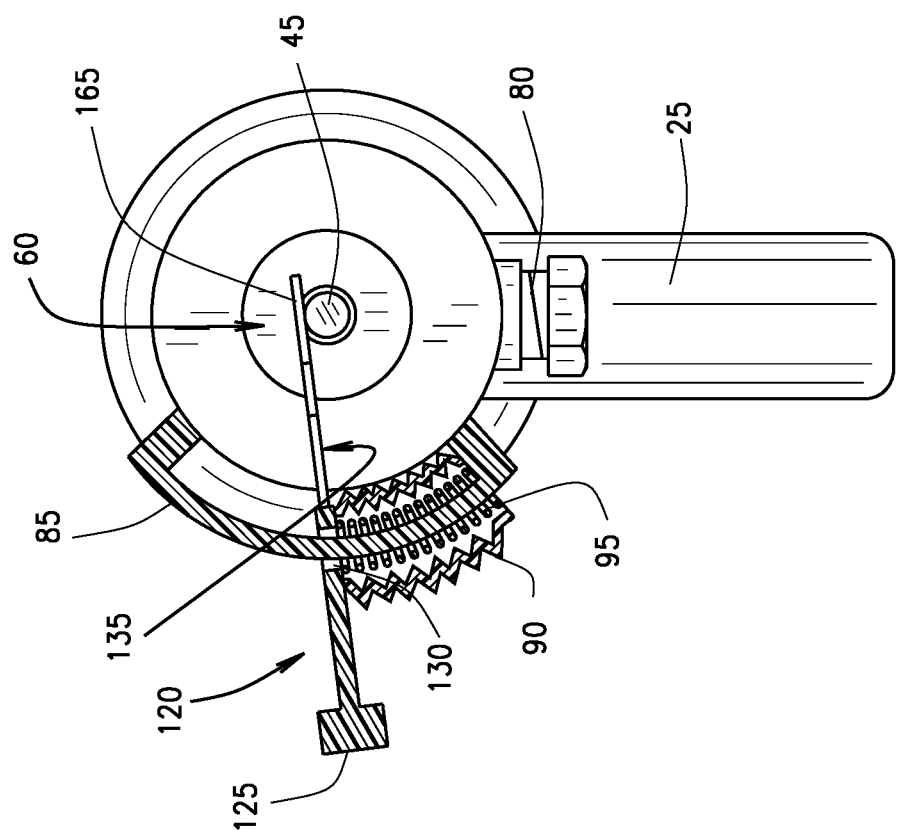
FIG. 4 is a front elevation view of the endoscope lens cleaning device of FIGS. 1-3 in a resting position.

An endoscope lens cleaning device is provided that may be coupled with an endoscope commonly known and understood in the art. Like most endoscopes, the endoscope with which the endoscope lens cleaning device may be coupled is used to generate clear images of small areas inside of patients during surgery. FIG. 1 illustrates an example endoscope 1 and an endoscope lens cleaning device 5 (hereinafter referred to as "cleaning device 5") that is selectively engageable with the endoscope 1 in a manner described in greater detail herein below.

The endoscope 1 includes each of a proximal portion 10 and a distal portion 15. At the proximal portion 10, the endoscope 1 preferably includes an eyepiece 20 through which a surgeon may view a surgical site with increased clarity. A light post 25 is preferably located somewhat distal relative to the proximal portion 10. The light post 25 preferably protrudes outwardly from the endoscope 1. The light post 25, which is constructed in accordance with other light posts known and understood in the art, is preferably able to receive and transmit light from an external light source that is connected with the light post 25. The light post 25 preferably includes optical light sources and fibers that help to provide light within the endoscope 1 that allows an operator to better see the surgical site.

A block member 30 is preferably provided near the light post 25 at a location along the length of the endoscope 1 near the light post 25. The block member 30 preferably has a distal face 35 from which a rod lens 40 may extend toward the distal portion 15 of the endoscope 1. The rod lens 40 preferably extends from the distal face 35 of the block member 30 to the distal portion 15 of the endoscope 1. The rod lens 40 is designed such that a surgeon using the endoscope 1 may see through the endoscope 1 beginning at the eyepiece 20 and extending through the block member 30 and the rod lens 40 and subsequently through a distal lens 45 located at the distal portion 15 of the endoscope 1. The distal lens 45 preferably includes a glass or otherwise transparent cover that prevents fluid and other materials at the surgical site from penetrating the lens 45 and entering the endoscope 1. In a preferred embodiment, the lens 45 is flat, or zero degrees, relative to the rod lens 40. In other words, the lens 45 is preferably perpendicular to the rod lens 40. In alternative embodiments, the lens 45 may be positioned at an alternative angle relative to the rod lens 40.

The cleaning device 5 is also illustrated in FIG. 1, as well as FIGS. 2 and 3, where the endoscope 1 is shown as inserted into and received by the cleaning device 5. The cleaning device 5, like the endoscope 1 includes each of a proximal portion 50 and a distal portion 55. Those proximal and distal portions 40, 55 are positioned such that they substantially line up with the proximal and distal portions 10, 15, respectively, of the endoscope 1, when the endoscope 1 is slid into the cleaning device 5. To do so, the proximal portion 50 of the cleaning device preferably includes an opening (not illustrated) through which the endoscope 1 may be inserted, starting with its distal portion 15.

Thus, when inserting the endoscope 1 into the cleaning device 5, the distal lens 45 and rod lens 40 may first be passed through the opening in the proximal portion 50 of the cleaning device 5. Then, the rod lens 40 may be inserted into the cleaning device 5 (which is substantially hollow from its proximal portion 50 to its distal portion 55) until the distal lens 45 in substantial alignment with an open end portion 60 of the cleaning device 5.

Upon alignment with the end portion 60, the rod lens 40 may be substantially contained within an elongated rod lens sheath 65. The rod lens sheath 65 is located near the distal portion 55 of the cleaning device 5 so that it is able to receive and secure the rod lens 40, which is also located toward the distal portion 15 of the endoscope 1. As such, the rod lens sheath 65 and the rod lens 40 may be substantially similar in shape as one another, with the sheath 65 having a diameter just larger than that of the rod lens 40, so that the rod lens 40 is snugly contained within the sheath 65, but the sheath 65 does not occupy too much space in a surgical site.

Moving closer to the proximal portion 50 of the cleaning device 5, the cleaning device 5 includes a first chamber 70 and a second chamber 75. The chamber 70 may substantially abut the rod lens sheath 65, with the rod lens sheath 65 being distal relative to the first chamber 70. The second chamber 75 is illustrated as having a diameter greater than that of the first chamber 70, and it is illustrated as proximal to the first chamber 70. In the illustrated embodiment, the distal face 35 of the block member 30 preferably abuts the first chamber 70 nearest the proximal portion 50 when the endoscope 1 is fully inserted into the cleaning device 5.

Both the first chamber 70 and the second chamber 75 in the illustrated endoscope 1 are configured for use with a particular endoscope (the Karl-Storz Hopkins rigid rod 0 degree endoscope) and particular components associated therewith. In alternative embodiments, the cleaning device 5 may take on different shapes and sizes to receive and secure various types of endoscopes therein.

An irrigation port 80 may also be provided on the cleaning device 5. In the illustrated embodiment, the irrigation port 80 is shown as extending downwardly from the first chamber 70. The irrigation port 80 is preferably designed to be compatible with any thin tube of a diameter of a size made to attach to the irrigation port 80 at a first end and to existing irrigation technology (e.g., the Medtronic EndoScrub), a generic pedal-activated saline pump, or even a simple syringe filled with saline at a second end.

The distal portion 55 of the cleaning device 5 beginning near the port 80 (or another port when used with a different endoscope) preferably includes a distal inner diameter only slightly larger than the diameter of the rod lens 40 and the distal lens 45 (on the scale of a fraction of a millimeter). Preferably, fluid pumped through the irrigation port 80 may travel the length of the cleaning device 5 in the space (not illustrated) between the surface of the rod lens 40 and the inside of the cleaning device 5. As fluid flows out the end portion 60 of the cleaning device 5, the fluid preferably falls over the lens 45. Then, the fluid may be used to better wipe the distal lens 45 in the manner described in greater detail herein below.

The spring-loaded mechanism that allows an operator to rapidly and effectively clean the distal lens 45 to increase surgical site visibility is shown in greater detail in FIGS. 2 and 3. A curved support rail 85 may be integrally formed with the second chamber 75. In alternative embodiments, the support rail 85 may be removably attached to the second chamber 75. Alternatively, when the cleaning device 5 is used with other types of endoscopes, it may be located elsewhere on the cleaning device 5. The support rail 85 may take on alternative shapes and forms, but in any form it should be long enough such that an elastic element may be placed around it.

FIG. 2 illustrates a cylindrically-shaped elastic sleeve 90 through which the support rail 85 extends. The elastic sleeve 90 is preferably flexible and thus can be made of a variety of materials, including plastic. The elastic sleeve 90 preferably surrounds and protects an elastic member 95 (shown in FIG. 3) that also surrounds the support rail 85. In FIG. 3, the elastic member 95 is embodied as a spring, but in alternative embodiments, it could be any form of an elastic element. The elastic sleeve 90 has been removed in FIG. 3 so that the spring 95 is more clearly illustrated, but in alternative embodiments, the elastic sleeve 90 may not be included as part of the mechanism. Alternatively, in other embodiments, the elastic sleeve 90 may serve as the elastic member, and no additional elastic member such as spring 95 may be necessary.

At an upper end 100 of the support rail 85, the support rail 85 includes a bent portion 105 that connects the support rail 85 to the second chamber 75 near the upper end 100. Similarly, at a lower end 110 of the support rail 85, the support rail 85 includes a bent portion 115 that connects the support rail 85 to the second chamber 75 near the lower end 110. The bent portions 105 and 115 preferably act as upper and lower limits in which the elastic sleeve 90 and/or the elastic member 95 is constrained and secured. In the illustrated embodiments, the bent portions 105, 115 are at substantially right angles relative to the support rail 85, but in alternative embodiments, may be disposed at other angles. Alternatively, other "stoppers" used to retain the elastic sleeve 90 and/or the spring 95 may be provided.

A toggle device 120 that compresses and decompresses the elastic sleeve 90 and/or the spring 95 is also shown in FIGS. 2 and 3. The toggle device 120 preferably includes a toggle switch 125 and an actuator 130 that extends outwardly from the actuator 130. The actuator 130 preferably includes a central aperture (not illustrated) that allows it to slide along the length of the support rail 85, but not the bent portions 105, 115 (or other "stoppers" in alternative embodiments).

A longitudinal rod 135 preferably extends from the actuator 130 to the distal portion 55 of the cleaning device 5. In the illustrated embodiment (because of the configuration of the endoscope), the rod 135 includes a first portion 140 that abuts the second chamber 75, a second portion 145 that abuts the first chamber 70, and a third portion 150 that abuts the rod lens sheath 65. The first and second portions 140, 145 are preferably connected to one another by connection rod 155, and the second and third portions 145, 150 are preferably connected by a connection rod 160, respectively. The connection rods 155, 160 are substantially perpendicular to the first, second, and third portions 140, 145, 150. In alternative embodiments, depending on the size and shape of the endoscope associated with the cleaning device 5, the longitudinal rod 135 may be continuous, or it may include any number of portions like those described above that allow it to extend to the distal portion 55 of the cleaning device 5. In such an embodiment, the connection rods 155, 160 may not be necessary.

At its most distal portion, the rod 135 preferably includes a wiper member 165 that projects perpendicularly inward from the third portion 150. The wiper member 165 is preferably made from a silicone or a rubber, and is not harmful to tissue, blood, etc. at a surgical site. The wiper member 165 is preferably at least as long as the diameter of the end portion 60. That way, when the wiper member 165 is activated in the manner described below, it preferably is able to wipe the entire surface area of the distal lens 45, which is preferably flush with the end portion 60 of the cleaning device 5. In the illustrated embodiment, the wiper member 165 is perpendicular to the rod 135, but that is because the distal lens 45 of the endoscope 1 is similarly perpendicular to the rod 135. If the distal lens 45 were at a different angle relative to the rod 135, the wiper member 165 would be disposed at substantially that same angle so that it would be flush with the distal lens 45 when activated using the mechanism described below.

Figure 5:
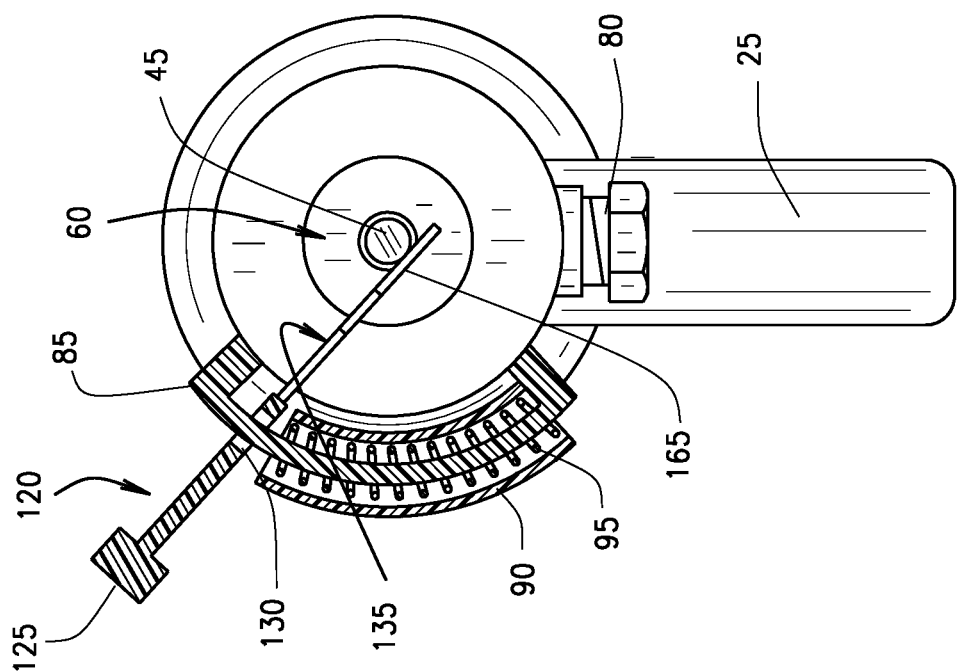
FIG. 5 is a front elevation view of the endoscope lens cleaning device of FIGS. 1-4 in an activated position.

It is possible that an operator could be holding the endoscope 1 and cleaning device 5 with one hand and simultaneously using a thumb to activate the below described wiping mechanism. FIGS. 4 and 5 illustrate the endoscope 1 and the cleaning device in a rear elevation view. In those drawings, a reader is looking from the distal portions 15, 55 of the endoscope 1 and cleaning device toward their proximal portions 10, 50. In those drawings, the toggle device 120 and the support rail 85 are shown in cross-section. The remainder of the endoscope 1 and cleaning device 5 is completely shown.

To activate the wiper member 165 to subsequently clean the distal lens 45 and the area surrounding it, a user should use his or her thumb (or other finger if easier) to press downwardly on the toggle switch 125. By doing so, the actuator 130 is also preferably pushed downwardly. The downward motion of the actuator 130 preferably compresses the elastic sleeve 90 and/or the spring 95, depending on the embodiment (and whether it includes one or both of the sleeve 90 and spring 95). The downward motion also preferably causes the longitudinal rod 135 to rotate downwardly, in a counter-clockwise direction. When the rod 135 rotates in a counter-clockwise direction, the wiper member 165 also preferably swivels about the axis of the rod 135 in a counter-clockwise direction. With that same motion, the wiper member 165 preferably wipes over the end portion 60 of the cleaning device 5, while in contact with the distal lens 45 of the endoscope 1, thus cleaning the surface of the lens 45, as shown in FIGS. 3 and 5. This preferably gives the operator a clearer view of the surgical site.

When an operator stops exerting a force on the toggle switch 125, the sleeve 90 and/or spring 95 may induce a clockwise force in the actuator 130, returning the actuator 130, rod 135, and wiper member 165 to the positions in which they began, the resting positions shown in FIGS. 2 and 4. Those positions are preferably clear from field of vision of the lens. The sleeve 90 and/or spring 95 thus may serve two purposes: 1) they alleviates responsibility of an operator to return the wiper member 165 to a location that does not obstruct vision of the distal lens 45 after wiping, and 2) it results in a second wiping motion that may help clear any additional obstructions as the wiper member 165 travels along the path to its resting position. While operating the cleaning device 5, an operator may from time to time utilize the irrigation system described above to facilitate the wiping process.

From the foregoing, it will be seen that the various embodiments of the present invention are well adapted to attain all the objectives and advantages hereinabove set forth together with still other advantages which are obvious and which are inherent to the present structures. It will be understood that certain features and sub-combinations of the present embodiments are of utility and may be employed without reference to other features and sub-combinations. Since many possible embodiments of the present invention may be made without departing from the spirit and scope of the present invention, it is also to be understood that all disclosures herein set forth or illustrated in the accompanying drawings are to be interpreted as illustrative only and not limiting. The various constructions described above and illustrated in the drawings are presented by way of example only and are not intended to limit the concepts, principles and scope of the present invention.

As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required".

Many changes, modifications, variations and other uses and applications of the present invention will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. An endoscope lens cleaning device for coupling with an endoscope, the endoscope lens cleaning device comprising:
   a sheath including an opening at a proximal portion of the endoscope lens cleaning device through which the endoscope may be inserted, the sheath further including an outer surface;
   an open end portion at a distal portion of the sheath of the endoscope lens cleaning device that is in substantial alignment with a distal lens of the endoscope when the endoscope is inserted into the endoscope lens cleaning device;
   a support rail located near the proximal portion of the endoscope lens cleaning device and projecting outwardly from the outer surface of the sheath of the endoscope lens cleaning device;
   an elastic member and/or an elastic sleeve surrounding the support rail;
   an actuator in communication with the elastic member and/or the elastic sleeve;
   a longitudinal rod coupled with the actuator, the longitudinal rod extending from the actuator to the distal portion of the endoscope lens cleaning device;
   a wiper member located at a distal portion of the longitudinal rod; and
   wherein when the actuator is depressed, the elastic member and/or the elastic sleeve are depressed, and the longitudinal rod is rotated, and the wiper member rotates in the same direction as the longitudinal rod so that the wiper member wipes the distal lens.

2. The endoscope lens cleaning device of claim 1 wherein when the actuator is released, tension from the elastic member and/or the elastic sleeve causes the actuator, longitudinal rod, and the wiper member to return to a resting position.

3. The endoscope lens cleaning device of claim 1 wherein the wiper member is made of silicon.

4. The endoscope lens cleaning device of claim 1 wherein the elastic member is a spring.

5. The endoscope lens cleaning device of claim 4 wherein the support rail is surrounded by the spring and the elastic sleeve, with the elastic sleeve surrounding the spring.

6. The endoscope lens cleaning device of claim 1 wherein the elastic sleeve is made of a flexible plastic.

7. The endoscope lens cleaning device of claim 1 wherein the endoscope lens cleaning device further includes an irrigation port through which fluid may be drawn.

8. The endoscope lens cleaning device of claim 7 wherein the endoscope lens cleaning device includes an elongated rod lens sheath having a diameter slightly larger than a rod lens of the endoscope, thus creating a space between the rod lens sheath and the rod lens.

9. The endoscope lens cleaning device of claim 8 wherein the space between the rod lens sheath and the rod lens is in fluid communication with the irrigation port at a first proximal end and in communication with the distal portion of the endoscope lens cleaning device at a second end.

10. The endoscope lens cleaning device of claim 1 wherein the wiper member has a diameter greater than the diameter of the distal lens of the endoscope.

11. An endoscope lens cleaning device for coupling with an endoscope, the endoscope lens cleaning device comprising:
    a sheath including an opening at a proximal portion of the endoscope lens cleaning device through which the endoscope may be inserted;
    an open end portion of the sheath at a distal portion of the endoscope lens cleaning device that is in substantial alignment with a distal lens of the endoscope when the endoscope is inserted into the endoscope lens cleaning device;
    a support rail located near the proximal portion of the endoscope lens cleaning device and projecting outwardly from the endoscope lens cleaning device;
    at least one of an elastic member surrounding the support rail;
    an actuator in communication with the elastic member;
    a rod attached to the actuator and extending from the actuator to the distal portion of the endoscope lens cleaning device;
    a wiper member located at a distal portion of the rod and extending inwardly from the rod; and
    wherein when the actuator is depressed, the elastic member is depressed, and the rod is rotated, and the wiper member rotates in the same direction as the rod so that the wiper member wipes the distal lens.

12. The endoscope lens cleaning device of claim 11 wherein when the actuator is released, tension from the elastic member causes the actuator, rod, and the wiper member to return to a resting position.

13. The endoscope lens cleaning device of claim 11 wherein the wiper member is made of silicon.

14. The endoscope lens cleaning device of claim 11 wherein the elastic member is a spring.

15. The endoscope lens cleaning device of claim 14 wherein an elastic sleeve surrounds the spring.

16. The endoscope lens cleaning device of claim 15 wherein the elastic sleeve is made of a flexible plastic.

17. The endoscope lens cleaning device of claim 11 wherein the endoscope lens cleaning device further includes an irrigation port through which fluid may be drawn.

18. The endoscope lens cleaning device of claim 17 wherein the endoscope lens cleaning device includes an elongated rod lens sheath having a diameter slightly larger than a rod lens of the endoscope, thus creating a space between the rod lens sheath and the rod lens.

19. The endoscope lens cleaning device of claim 18 wherein the space between the rod lens sheath and the rod lens is in fluid communication with the irrigation port at a first proximal end and in communication with the distal portion of the endoscope lens cleaning device at a second end.

20. The endoscope lens cleaning device of claim 11 wherein the wiper member has a diameter greater than the diameter of the distal lens of the endoscope.

* * * * *